United States Patent [19]

D'Amico

[11] 4,049,419
[45] Sept. 20, 1977

[54] USE OF BENZOTHIAZOLINE COMPOUNDS AS PLANT GROWTH REGULANTS

[75] Inventor: John J. D'Amico, St. Louis, Mo.

[73] Assignee: Monsanto Company, St. Louis, Mo.

[21] Appl. No.: 660,741

[22] Filed: Feb. 26, 1976

Related U.S. Application Data

[63] Continuation-in-part of Ser. No. 576,512, May 12, 1975, Pat. No. 3,993,468.

[51] Int. Cl.² .................................................. A01N 9/12
[52] U.S. Cl. .......................................... 71/76; 71/90;
260/304 R
[58] Field of Search ...................................... 71/90, 76

[56] References Cited

U.S. PATENT DOCUMENTS

3,839,349  10/1974  Wagner et al. ...................... 71/67 X

FOREIGN PATENT DOCUMENTS

21,378  6/1971  Japan .................................... 71/90
10,182  3/1973  Japan .................................... 71/90

*Primary Examiner*—Lewis Gotts
*Assistant Examiner*—Catherine L. Mills
*Attorney, Agent, or Firm*—Richard H. Shear; Donald W. Peterson

[57] ABSTRACT

Certain benzothiazoline compounds are found to have plant growth regulation activity on leguminous plants.

29 Claims, No Drawings

USE OF BENZOTHIAZOLINE COMPOUNDS AS PLANT GROWTH REGULANTS

This application is a continuation-in-part of Ser. No. 576,512 filed May 12, 1975 now U.S. Pat. No. 3,993,468.

This invention relates to the regulation of leguminous plant growth by application of an effective amount of certain benzothiazoline compounds to the plant. More specifically, this invention is concerned with the alteration of the canopy of leguminous plants, e.g. soybean, in order to allow better penetration of light into the canopy.

Much research is being conducted to develop methods for increasing the yield of crop plants. Leguminous plants have canopies that effectively inhibit sunlight from reaching the lower leaves. For example, the canopy of soybeans is such that approximately 85 percent of the sunlight is absorbed by the outer layer of leaves. Many researchers feel that by altering the canopy of soybeans so that light falls more deeply into the canopy, yields could be increased. Weber, in Field Crop Abstracts, Vol. 21, No. 4, pages 313-317, states that "greater light penetration, resulting in greater amount of the [soybean] plant canopy having a light intensity above 150 f.c., generally led to higher seed yields." Johnson et al, in Crop Science, Vol. 9, pages 577–581, states that "adding light increased the yields of bottom, middle and top canopy positions of [soybean] plants 30, 20 and 2%, respectively." Thus, it would be highly beneficial if a method was found whereby the canopy of such plants could be altered such that a greater number of leaves could be illuminated.

It is an object of the invention to provide a method of altering the canopy of leguminous plants such that light penetration into the canopy is enhanced.

It is further an object of the invention to regulate the growth of leguminous plants by means of a chemical treatment.

These and other objects, not specifically mentioned, are accomplished by treating said leguminous plants with the hereinafter-described benzothiazoline compounds.

The term "plant regulant" or "plant growth regulant", as employed in this application, connotes a material which serves to modify the normal sequential development of a treated plant to agricultural maturity. Such modification may result from the effect of material on the physiological processes of the plant or from the effect of said material on the morphology of the plant. It should additionally be recognized that modifications may also result from a combination or sequence of both physiological and morphological factors.

Modifying effects of a plant regulant are probably most readily observed as changes in the size, shape, color or texture of the treated plant or any of its parts. Similarly, changes in the quantity of the plant fruit or flowers are also quite apparent from simple, visual inspection. The above changes may be characterized as an acceleration or retardation of plant growth, stature reduction, leaf or canopy alternation, increased branching, terminal inhibition, increased flowering or fruit set.

Modifications in the normal sequential development of a treated plant to agricultural maturity may also be manifested by reduced transpiration or increased carbohydrate deposition or protein content.

It is to be understood that the regulation of plants in accordance with the instant invention does not include the total inhibition or the killing of such plants. Although phytotoxic acmounts of the materials disclosed herein might be employed to exert a herbicidal (killing), action it is contemplated herein to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amount will vary, not only with the material selected, but also with the modifying effect desired, the species of plant and its stage of development, the plant growth medium and whether a permanent or transitory effect is sought.

It is presently known that certain benzothiazyl compounds possess herbicidal activity. U.S. Pat. No. 3,069,429 discloses the use of derivatives of 4-halogeno-2-oxobenzothiazolin-3-ylacetic acid to kill weeds. U.S. Pat. No. 3,651,074 discloses the use of certain 2-oxo-3-benzothiazolines as a herbicide. Neither of these patents, however, disclose the use of the specific benzothiazolines used in accordance with the present invention to regulate the growth of plants. Further, neither of these patents disclose the use of such benzothiazolines to alter the canopy of leguminous plants.

It is further known that certain benzothiazyl compounds possess plant growth regulating activity. U.S. Pat. No. 2,468,075 discloses the use of such compounds as abscission agents. Japanese Pat. No. 71/21378 discloses that such compounds possess plant growth regulating activity, but does not disclose any specific uses. Japanese Pat. No. 73/10182 discloses the use of benzothiazyl compounds as grafting agents for tree root growth.

The prior art does not teach, however, the use of the compounds of the invention as plant growth regulating agents for soybean. Further, the prior art was unaware that application of said compounds to soybeans altered the canopy of the plant such that light penetration into the canopy is enhanced. Finally, the prior art was unaware of the increase in yield obtainable by treating soybeans with the benzothiazoline compounds of the invention.

THE PLANT GROWTH REGULATING COMPOUNDS

The plant growth regulating compounds of the present invention have a chemical structure represented by the following formula

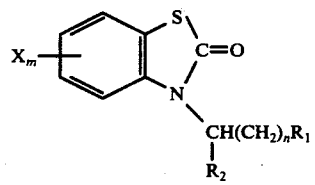

(I)

wherein X is halo; $m$ is 0 or 1;

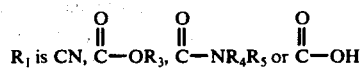

$R_1$ is CN, $\overset{O}{\overset{\|}{C}}-OR_3$, $\overset{O}{\overset{\|}{C}}-NR_4R_5$ or $\overset{O}{\overset{\|}{C}}-OH$ and agriculturally acceptable salts thereof; $R_2$ is H, CN, lower alkyl or

$R_3$ is lower alkyl; $R_4$ and $R_5$ are independently H, alkyl or when taken together form a heterocyclic ring having up to 8 carbon atoms; and n is 0 or 2; provided that $R_2$ is

only when $R_1$ is

and n is 0. Preferably, $R_2$ is H.

The term "agriculturally acceptable salts" is understood by mean alkali metal, substituted amine, such as isopropyl amine, and triethylamine, and ammonium salts. The term "lower" alkyl is understood to mean those alkyl groups having from 1 to 5 carbon atoms, inclusive.

As a means of illustration the following compounds have been found to be effective as plant growth regulants.

A. 2-oxo-3-benzothiazoline acetonitrile
B. 2-oxo-3-benzothiazoline butyronitrile
C. 5-chloro-2-oxo-3-benzothiazoline acetonitrile
D. 4-chloro-2-oxo-3-benzothiazoline acetonitrile
E. Methyl-2-oxo-3-benzothiazoline acetate
F. Ethyl-2-oxo-3-benzothiazoline acetate
G. Butyl-2-oxo-3-benzothiazoline acetate
H. Ethyl-4-chloro-2-oxo-3-benzothiazoline acetate
I. Ethyl-α-methyl-2-oxo-3-benzothiazoline acetate
J. Ethyl-5-chloro-2-oxo-3-benzothiazoline acetate
K. Ethyl-5-chloro-α-methyl-2-oxo-3-benzothiazoline acetate
L. 2-oxo-3-benzothiazoline acetic acid
M. 4-chloro-2-oxo-3-benzothiazoline acetic acid
N. 5-chloro-α-methyl-2-oxo-3-benzothiazoline acetic acid
O. 5-chloro-2-oxo-3-benzothiazoline acetic acid
P. α-methyl-2-oxo-3-benzothiazoline acetic acid
Q. Diethyl-2-oxo-3-benzothiazoline malonate
R. Dimethyl-2-oxo-3-benzothiazoline malonate
S. Diethyl-5-chloro-2-oxo-3-benzothiazoline malonate
T. 2-oxo-3-benzothiazoline acetamide
U. N-methyl-2-oxo-3-benzothiazoline acetamide
V. Triethylamine salt of Compound (L)
W. Sodium salt of Compound (L)
X. Ammonium salt of Compound (L)
Y. Isopropylamine salt of Compound (L)

The above compounds may be prepared in accordance with Examples 1-14.

EXAMPLE 1

PREPARATION OF COMPOUNDS A AND C

A charge containing 0.5 mole of 2-benzothiazolol or 5-chloro-2-benzothiazolol, 33 g. (0.5 moles) of 85% potassium hydroxide and 300 ml. of acetone is stirred for 10 minutes. To the stirred solution is added in one portion 37.2 g. (0.5 mole) of chloroacetonitrile at 40° C. After a temperature rise to about 62° C., the stirred reaction mixture is heated at reflux for 6 hours and then at 25°-30° C. for 18 hours. After the addition of 700 ml. of water, stirring is continued for 30 minutes at 25°-30° C. The solid is then collected by filtration, washed with water until the washings were neutral to litmus and air-dried at 25°-30° C. The data are summarized in Table I.

EXAMPLE 2

PREPARATION OF COMPOUND B

A charge containing 30.2 g. (0.2 mole) of 2-benzothiazolol, 13.2 g. (0.2 mole) of 85 percent potassium hydroxide, 200 ml. of dimethylformamide and 15 ml. of water is stirred for 10 minutes. To the stirred solution at 38° C., 22.8 g. (0.2 mol) of 4-chlorobutyronitrile is added in one portion and then heated at 90°-100° C. for 29 hours. After stirring at 25°-30° C. for 18 hours, 600 ml. of water and 600 ml. of ethyl ether are added and stirring continued for 15 minutes. The separated ether layer is washed with water until the washings were neutral to litmus and dried over sodium sulfate. The ether was removed in vacuo at maximum temperature of 80°-90° C. at 1-2 mm. The data are summarized in Table I.

EXAMPLE 3

PREPARATION OF COMPOUND D

To a stirred slurry containing 37.2 g. (0.2 mole) of 4-chloro-2-benzothiazolol, 28 g. (0.2 mol) of potassium carbonate and 300 ml. of acetone, 16.6 g. (0.22 mole) of chloroacetonitrile is added in one portion and then heated at reflux (55°-57° C.) for 3 hours. After cooling at 25° C., 700 g. of ice water is added and stirring continued for 1 hour at 0°-20° C. The solid is then collected by filtration, washed with water until the washings were neutral to litmus and air-dried at 45° C. The data are summarized in Table I.

TABLE I

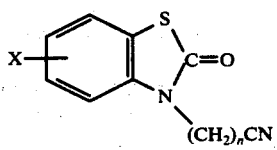

| Compound | X | n | mp. ° C. | % Yield | % Cl Calcd. | % Cl Found | % N Calcd. | % N Found | % S Calcd. | % S Found |
|---|---|---|---|---|---|---|---|---|---|---|
| A | H | 1 | 135-136[a] | 95 | — | — | 14.73 | 14.65 | 16.86 | 17.01 |
| B | H | 3 | viscous liquid | 69 | — | — | 12.84 | '12.72 | 14.69 | 14.92 |
| C | 5-Cl | 1 | 186-187[b] | 95 | 15.78 | 15.94 | 12.47 | 12.44 | 14.27 | 14.50 |

TABLE I-continued

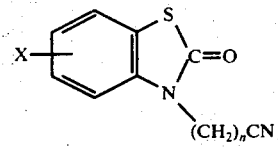

| Compound | X | n | mp. °C. | % Yield | % Cl Calcd. | % Cl Found | % N Calcd. | % N Found | % S Calcd. | % S Found |
|---|---|---|---|---|---|---|---|---|---|---|
| D | 4-Cl | 1 | 166–167[c] | 98 | 15.78 | 15.34 | 12.47 | 12.47 | 14.27 | 14.20 |

[a]Recrystallization from isopropyl alcohol.
[b]Recrystallization from toluene.
[c]Recrystallization from ethyl alcohol and benzene.

EXAMPLE 4

PREPARATION OF COMPOUNDS E and F

To a stirred solution containing 75.5 g. (0.5 mole) of 2-benzothiazolol, 33 g. (0.5 mole) of 85 percent potassium hydroxide, 300 ml. of methyl or ethyl alcohol and 20 ml. of water, is added 0.5 mole of methyl or ethyl chloroacetate. After heating at reflux for 24 hours, the stirred reaction mixture is cooled to 25° C. followed by the addition of 500 ml. of water. After stirring at 0°–10° C. for 2 hours, the solid is collected by filtration, washed with water until neutral to litmus and air-dried at 25°–30° C. The date are summarized in Table II.

EXAMPLE 5

PREPARATION OF COMPOUND G

A stirred charge containing 0.1 mole of 2-oxo-3-benzothiazoline acetic acid (Compound L), 75 ml. of butyl alcohol, 170 ml. of benzene and 2 drops of concentrated sulfuric acid is heated at reflux for 4 hours. By means of a Dean Stark condenser 1.8 ml. of water is removed during this heating period. The solvents (195 ml). are removed by distillation to a maximum pot temperature of 105° C. To the cooled stirred residue 400 ml. of water containing 0.1 mole of 50 percent aqueous sodium hydroxide and 500 ml. of ethyl ether are added. After stirring for 15 minutes, the separated ether layer is washed with water until neutral to litmus and dried over sodium sulfate. The ether is removed in vacuo at maximum temperature of 30 ° C. The solid is air-dried at 25°–30° C. on a porous plate. The data are summarized in Table II.

EXAMPLE 6

PREPARATION OF COMPOUNDS H, I, J AND K

To a stirred slurr containing 0.2 mole of 2-benzothiazolol or 4-chloro or 5-chloro-2-benzothiazolol, 28 g. (0.203 mole) of potassium carbonate and 300 ml. of acetone, 0.22 mol of ethyl bromoacetate or ethyl-2-bromo-propionate is added in one portion and then added at reflux for 4 hours. For Compounds H and J, after cooling to 0° C., 700 g. of ice water is added and stirring continued at 0°–20° C. for 30 minutes. The solid is collected by filtration, washed with water until neutral and air-dried at 25°–30° C. For compounds I and K, after cooling to 25° C., 400 ml of water and 500 ml. of ethyl ether are added and stirring continued for 15 minutes. The separated ether layer is washed with water until neutral to litmus and dried over sodium sulfate. The ether is removed in vacuo at maximum temperature of 80°–90° C. at 1–2 mm. The data are summarized in Table II.

TABLE II

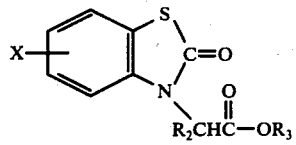

| Compound | X | $R_2$ | $R_3$ | Solvent | mp. °C. | % Yield | % Cl Calcd. | % Cl Found | % N Calcd. | % N Found | % S Calcd. | % S Found |
|---|---|---|---|---|---|---|---|---|---|---|---|---|
| E | H | H | —CH$_3$ | CH$_3$OH | 96–97[a] | 75 | — | — | 6.27 | 6.26 | 14.36 | 14.67 |
| F | H | H | —C$_2$H$_5$ | C$_2$H$_5$OH | 90–91[a] | 74 | — | — | 5.90 | 6.12 | 13.51 | 13.50 |
| G | H | H | —C$_4$H$_9$ | C$_4$H$_9$OH and C$_6$H$_6$ | 79–80[b] | 60 | — | — | 5.28 | 5.26 | 12.09 | 12.17 |
| H | 4-Cl | H | —C$_2$H$_5$ | CH$_3$COCH$_3$ | 83[a] | 99 | 13.05 | 12.70 | 5.16 | 4.95 | 11.80 | 11.59 |
| I | H | —CH$_3$ | —C$_2$H$_5$ | CH$_3$COCH$_3$ | viscous liquid | 98 | — | — | 5.57 | 5.41 | 12.76 | 12.55 |
| J | 5-Cl | H | —C$_2$H$_5$ | —CH$_3$COCH$_3$ | 115–116[b] | 99 | 13.15 | 13.36 | 5.16 | 5.13 | 11.80 | 12.37 |
| K | 5-Cl | —CH$_3$ | —C$_2$H$_5$ | —CH$_3$COCH$_3$ | viscous liquid | 98 | 12.41 | 12.55 | 4.90 | 4.84 | — | — |

[a]Recrystallization from ethyl alcohol
[b]Recrystallization from heptane

EXAMPLE 7

PREPARATION OF COMPOUND L

A stirred charge containing 37.8 g. (0.25 mol) of 2-benzothiazolol, 40 g. (0.25 mol) of 25 percent aqueous sodium hydroxide and 200 ml. of water is heated to 90° C. and filtered hot to remove a small amount of impurities. To a stirred solution containing 35 g. (0.25 mol) of bromoacetic acid in 100 ml. of water, 18.6 g. (0.125 mol) of potassium carbonate is added in small portions (foaming until a pH = 8 was obtained). This solution is added to the stirred solution of sodium 2-benzothiazolol and heated at 90°–100° C. for 6 hours and at 25°–30° C. for 18 hours. To this solution, 25 g. of concentrated hydrochloric in 500 ml. of water is added slowly until pH = 2 to 3 is obtained. After stirring, at 0°–20° C. for 30 minutes, the solid was collected by filtration, washed with water until neutral to litmus and air-dried at 45° C. The data are summarized in Table III.

EXAMPLE 8

PREPARATION OF COMPOUNDS M, N, O AND P

To a stirred refluxing solution containing 0.2 mole of the appropriate ester (Compound H, I, J or K) in 200 ml. of methyl alcohol, 34.4 g. (0.215 mole) of 25 percent aqueous sodium hydroxide in 165 ml. of water is added dropwise over a 30 minute period and then heated at reflux for 30 minutes. The methyl alcohol (180 ml.) is removed by distillation. The cooled residue is poured into 1 liter of water. To this stirred solution, 30 g. (0.3 mole) of concentrated hydrochloric acid is added dropwise unitl pH 2 or 3 is obtained. After stirring at 25°–30° C. for 1 hour, the solid is collected by filtration, washed with water until neutral to litmus and air-dried at 25°–30° C. The date are summarized in Table III.

acetone, 0.2 mole of diethyl or dimethyl bromomalonate is added in one portion. After additions, the temperature rises to 50° C. The reaction mixture is refluxed for 24 hours at 55°–56° C. After cooling to 25° C., 300 ml. of water and 500 ml. of ethyl ether are added to the reaction mixture and stirred for 15 minutes. The resulting mixture is filtered to remove impurities, and the ether layer of the filtrate recovered. The ether solution is washed with water until neutral and then dried over sodium sulfate. The ether is removed in vacuo at the maximum temperature of 50°–60° C. at 1–2 mm. Compound Q, an amber viscous liquid solidified upon standing at room temperature. The data are summarized in Table IV.

TABLE IV

| Compound | X | $R_3$ | mp. ° C. | % Yield | % Cl Calcd. | % Cl Found | % N Calcd. | % N Found | % S Calcd. | % S Found |
|---|---|---|---|---|---|---|---|---|---|---|
| Q | H | —$C_2H_5$ | 62–63 | 69 | — | — | 4.53 | 4.62 | 10.37 | 10.80 |
| R | H | —$CH_3$ | 92–94[a] | 72 | — | — | 4.98 | 4.81 | 11.40 | 11.25 |
| S | 5-Cl | —$C_2H_5$ | low melting | 89 | 10.31 | 10.34 | 4.07 | 3.80 | — | — |

[a]Recrystallization from isopropyl alcohol

TABLE III

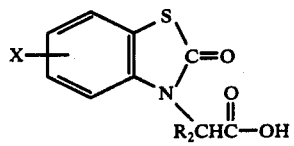

| Compound | X | $R_2$ | mp. ° C. | % Yield | % Cl Calcd. | % Cl Found | % N Calcd. | % N Found | % S Calcd. | % S Found |
|---|---|---|---|---|---|---|---|---|---|---|
| L | H | H | 184–185[a] | 83 | — | — | 6.70 | 6.75 | 15.33 | 15.08 |
| M | 4-Cl | H | 199–200[b] | 95 | 14.55 | 14.36 | 5.75 | 5.65 | 13.16 | 12.78 |
| N | 5-Cl | —$CH_3$ | 192–193[b] | 90 | 13.76 | 13.60 | 5.44 | 5.57 | 12.44 | 12.57 |
| O | 5-Cl | H | 250–251[c] | 95 | 14.55 | 14.10 | 5.75 | 5.98 | 13.16 | 13.07 |
| P | H | —$CH_3$ | 168–169[b] | 94 | — | — | 6.27 | 6.40 | 14.36 | 14.23 |

[a]Recrystallization from toluene-acetone
[b]Recrystallization from ethyl acetate
[c]Recrystallization from ethyl alcohol

EXAMPLE 9

PREPARATION OF COMPOUNDS Q, R AND S

To a stirred solution containing 0.2 mole of 2-benzothiazolol or 5-chloro-2-benzothiazolol and 13.2 g. (0.2 mole) of 85 percent potassium hydroxide in 250 ml. of

EXAMPLE 10

PREPARATION OF COMPOUNDS T AND U

To a stirred solution containing 30.3 g. (0.2 mole) of benzothiazolol, 13.2 g. (0.2 mol) of 85 percent potassium hydroxide in 250 ml. of acetone containing 20 ml. of water, 0.2 mole of 2-chloroacetamide or N-methyl-α-chloroacetamide is added in one portion. The stirred reaction mixture is heated at reflux for 5.5 hours and at 25°–30° C. for 18 hours. After the addition of 700 ml. of water, stirring is continued at 25°–30° C. for 30 minutes. The solid is collected by filtration, washed with water until the washings were neutral to litmus and air-dried at 25°–30° C. The date are summarized in Table V.

TABLE V

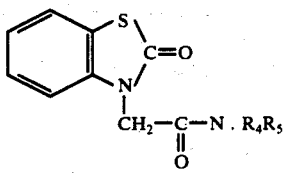

| Compound | R₄ | R₅ | mp. °C | % Yield | %N Calcd. | %N Found | %S Calcd. | %S Found |
|---|---|---|---|---|---|---|---|---|
| T | H | H | 253-254ᵃ | 79 | 13.45 | 13.61 | 15.40 | 15.62 |
| U | —CH₃ | H | 205-206ᵇ | 99 | 12.60 | 12.74 | 14.43 | 14.19 |

ᵃRecrystallization from isopropyl alcohol.
ᵇRecrystallization from methyl alcohol.

EXAMPLE 11

PREPARATION OF COMPOUND V

To a stirred slurry containing 20.9 g. (0.12 mole) of Compound L and 100 ml. of ethyl ether, 12.2 g. (0.12 mole) of triethyl amine is added in one portion. After stirring at 25°-30° C. for 2 hours, the ethyl ether and excess triethyl amine is removed in vacuo at maximum temperature of 80°-90° C. at 1-2 mm. The product, a dark amber viscous liquid, is obtained in 99 percent yield.

Anal. Calcd. for $C_{15}H_{22}N_2O_3S$: N, 9.03; S, 10.33. Found: N, 9.11; S, 10.90.

EXAMPLE 12

PREPARATION OF COMPOUND W

A charge containing 20.9 g. (0.1 mole) of Compound L, 4 g. (0.1 mole) of sodium hydroxide and 200 ml. of water is stirred for 2 hours to give a 100 percent yield of a 10.2 percent aqueous solution of the sodium salt of Compound L.

EXAMPLE 13

PREPARATION OF COMPOUND X

A charge containing 20.9 g. (0.1 mole) of Compound L, 6.1 g. (0.1 mole) of 58 percent ammonium hydroxide and 300 ml. of water is stirred for 3 hours to give a 100 percent yield of a 6.9 percent aqueous solution of the ammonium salt of Compound L.

EXAMPLE 14

PREPARATION OF COMPOUND Y

To a stirred slurry containing 20.9 g. (0.1 mole) of Compound L and 650 ml. of ethyl ether, 6.5 g. (0.11 mole) of isopropyl amine is added in one portion. After stirring at 25°-30° C. for 3 hours, the solid is collected by filtration and air-dried at 25°-30° C. The product, mp. 165°-167° C. is obtained is 88 percent yield. After recrystallization from methyl alcohol, it melted at 170°-171° C.

Anal. Calcd. for $C_{12}H_{16}N_2O_3S$: C, 53.71; H, 6.01; N, 10.44; S, 11.95. Found: C, 53.10; H, 5.87; N, 10.20; S, 11.69.

THE PLANT GROWTH REGULATING COMPOSITIONS AND METHOD

The term "active ingredient" is used in this specification to describe the active benzothiazolines of the foregoing formula. In practicing the plant growth regulating methods of this invention, the active ingredients can be used alone or in combination with a material referred to in the art as an adjuvant in liquid or solid form. The plant growth regulating compositions of this invention are prepared by admixing the active ingredient with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely divided particulate solid, a solvent liquid of organic origin, water, a wetting agent, dispersing agent, or emulsifying agent or any suitable combination of these.

When applying the active ingredient to leguminous plants, useful finely divided solid carriers and extenders include, for example, the talcs, clays, pumice, silica, diatomaceous earth, quartz, Fullers earth, sulfur, powdered cork, powdered wood, walnut flour, chalk, tobacco dust, charcoal and the like. Typical liquid diluents useful in applying the active ingredient to leguminous plants include for example, Stoddard solvent, acetone, alcohols, glycols, ethyl acetate, benzene and the like. Such leguminous plant growth regulating compositions, particularly liquids and wettable powders, usually contain as a conditioning agent one or more surface-active agents in amounts sufficient to render a given composition readily dispersible in water or in oil. By the term "surface-active agent" it is understood that wetting agents, dispersing agents, suspending agents and emulsifying agents are included therein. Such surface-active agents are well known and reference is made to U.S. Pat. No. 2,547,724, columns 3 and 4, for detailed examples of the same.

Compositions of this invention generally contain from about 5 to 95 parts active ingredient, about 1 to 50 parts surface-active agent and about 4 to 94 parts solvent, all parts being by weight based on the total weight of the composition.

It has been found that desirable modification of leguminous plants is achieved by applying the above-described plant regulants to seeds, emerging seedlings, roots, stems, leaves, flowers, fruits or other plant parts. Such application may be made directly to the plant part, or indirectly by application to the plant growing medium.

The application of liquid and particulate solid compositions of the active ingredient can be carried out by conventional techniques utilizing, for example, spreaders, power dusters, boom and hand sprayers and spray dusters. The compositions can also be applied from airplanes as a dust or spray. If desired, application of the compositions of the invention to leguminous plants can be accomplished by incorporating the compositions in the soil or other media in the area where modification of the plants is desired.

In selecting the appropriate non-toxic rate of application of the active ingredient to leguminous plants, it will be recognized that precise rates will also be dependent upon the mode of application, such as soil incorporation, band application, pre-plant seed treatment, result desired and various other factors known to those skilled in the art. At the higher rates the stature of the plant is significantly reduced. At lower rates, however, an alteration in the canopy of the plant is noted. To achieve such an alteration in canopy, foliar application rates of from 0.01 to 3.0 pounds of the active ingredient per acre (0.0112 to 3.36 kilos/hectare) are preferred. In applications to the soil habitat of germinant seeds, emerging seedlings, and established vegetation for the regulation of plant growth, the active ingredients are applied in amounts of from about 0.05 to about 20 pounds per acre or more (0.056 to 22.4 kilos/hectare). Preferably, the active ingredients are applied to the soil at a rate of from 0.1 to 5 pounds per acre (0.112 to 5.56 kilos/hectare). Foliar application to plants beginning to blossom are particularly advantageous and are preferred.

The following examples are presented to illustrate the variety of regulatory responses observed when the benzothiazoline compounds of the invention are applied to soybean plants at various rates.

In accordance with the practice of the invention, plant growth regulating compositions were formulated utilizing the active ingredient. The compositions to be used on soybean were formulated so that an effective amount of active ingredient could be applied at a rate the equivalent of 200 gallons per acre (302 liters/hectare). Table VI illustrates the formulation of the composition for several application rates of active ingredient. In each formulation, the stock solution utilized is 1% of the active ingredient dissolved in acetone.

TABLE VI

| RATE Lbs/Acre (kilos/hectare) | ml. of 1% Stock Solution | ml. Acetone | ml. 0.39% TWEEN 20 In Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |
| 0.3 (.336) | 0.1 | 1.9 | 3.6 |

EXAMPLE 15

A number of soybean plants are grown from seeds in aluminum pans in the greenhouse for a period of approximately 1 week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with TABLE VI is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and 2 weeks after application represents the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction, or an increase in growth in excess of 25% of that of the control plants, i.e., growth stimulation.

TABLE VII below summarizes the results and observations made in accordance with Example 15 when the benzothiazolines of the invention were utilized as the active ingredient at several rates.

TABLE VII

| Compound | RATE Lbs/Acre (kilos/hectare) | Results |
|---|---|---|
| A | 6.0 (6.72) | Stature reduction, leaf alteration, thick leaf texture, inhibition of apical development, axillary bud development, slight leaf burn |
|  | 3.0 (3.36) | Axillary bud development, leaf alteration, thick leaf texture, slight leaf burn |
|  | 1.2 (1.34) | Leaf alteration, thick leaf texture, slight leaf burn |
| B | 6.0 (6.72) | Stature reduction, leaf distortion, leaf inhibition, slight leaf burn |
| L | 6.0 (6.72) | Stature reduction, stem distortion, leaf distortion, slight leaf burn |
|  | 6.0 (6.72) | Stature reduction, stem distortion, epinasty, inhibition of apical development |
|  | 3.0 (3.36) | Stature reduction, stem distortion, inhibition of apical development |
|  | 3.0 (3.36) | Stature reduction, epinasty, stem distortion, inhibition of apical development |
|  | 1.2 (1.34) | Stature reduction, stem distortion, inhibition of apical development |
|  | 0.6 (0.672) | Stature reduction, stem distortion, inhibition of apical development |
| Q | 1.2 (1.34) | Stature reduction, axillary bud development, leaf alteration |
|  | 3.0 (3.36) | Stature reduction, stem distortion, inhibition of apical development, axillary bud development, leaf inhibition, slight leaf burn |
|  | 1.2 (1.34) | Stature reduction, stem distortion, epinasty, inhibition of apical development |
|  | 0.6 (0.672) | Stature reduction, stem distortion, inhibition of apical development |
|  | 3.0 (3.36) | Stimulation, stem distortion, leaf inhibition, inhibition of apical development |
|  | 0.3 (0.336) | Stature reduction, epinasty, stem distortion, leaf inhibition, inhibition of apical development |
|  | 0.6 (0.67) | Axillary bud development, leaf alteration, leaf inhibition |
|  | 0.12 (0.134) | Axillary bud development, leaf alteration, leaf inhibition, inhibition of apical development |
| E | 6.0 (6.72) | Stature reduction, slight leaf burn, stem distortion, leaf distortion |
|  | 3.0 (3.36) | Stature reduction, axillary |

TABLE VII-continued

| Compound | RATE Lbs/Acre (kilos/hectare) | Results |
|---|---|---|
|  |  | bud development, stem distortion, inhibition of apical development |
|  | 6.0 (6.72) | Stature reduction, stem distortion, inhibition of apical development |
|  | 3.0 (3.36) | Stature reduction, axillary bud development, stem distortion, leaf inhibition, inhibition of apical development |
|  | 1.2 (1.34) | Stature reduction, axillary bud development, stem distortion, leaf inhibition, inhibition of apical development |
|  | 0.6 (0.672) | Stature reduction, axillary bud development, stem distortion, leaf inhibition, inhibition of apical development |
|  | 0.3 (0.336) | Stature reduction, chlorosis, axillary bud development, stem distortion, leaf alteration, inhibition of apical development |
|  | 0.12 (0.134) | Axillary bud development, leaf alteration, leaf inhibition, inhibition of apical development |
| R | 6.0 (6.72) | Stature reduction, stem distortion, leaf inhibition, inhibition of apical development |
| T | 6.0 (6.72) | Stature reduction, axillary bud development, leaf alteration, leaf inhibition, inhibition of apical development |
|  | 6.0 (6.72) | Stature reduction, slight leaf burn, epinasty, stem distortion, leaf distortion, inhibition of apical development. |
|  | 3.0 (3.36) | Stature reduction, epinasty, stem distortion, leaf distortion, inhibition of apical development |
|  | 1.2 (1.34) | Stature reduction, leaf distortion, leaf inhibition, inhibition of apical development |

EXAMPLE 16

The procedure of Example 15 was repeated utilizing, however, the plant growth regulation composition below.

|  | % by weight |
|---|---|
| 2-oxo-3-benzothiazoline acetonitrile | 25.0 |
| Aerosol OTB | 4.0 |
| Reax 45A | 4.0 |
| Burden Clay | 67.0 |
|  | 100.0 |

The results are summarized in Table VIII.

TABLE VIII

| RATE Lbs/Acre (kilos/hectare) | Results |
|---|---|
| 1.0 (1.12) | Leaf distortion, early pod set, axillary bud inhibition |
| 0.5 (0.560) | Leaf distortion, early pod set |
| 0.25 (0.28) | Early pod set |
| 1.0 (1.12) | Leaf distortion, leaf alteration, early pod set |
| 0.5 (0.560) | Leaf alteration |
| 0.25 (0.28) | Leaf alteration |

Further examples illustrate the leaf alteration is obtained when the compounds are applied at lower rates.

EXAMPLE 17

Individual soybean plants are grown from seed in 6-inch pots containing a good grade of top soil. Two pots of 6-week old plants (5-6 trifoliate stage) are used for each application of the chemical. An overhead spary of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations made utilizing the test procedure of Example 17 are summarized in Table IX.

TABLE IX

| Compound | RATE Lbs/Acre (kilos/hectare) | Results |
|---|---|---|
| A | 2.5 (2.80) | Stature reduction, necrosis, leaf distortion, leaf inhibition, early pod set, enhanced pod set |
|  | 1.0 (1.12) | Stature reduction, necrosis, leaf alteration, leaf inhibition, early pod set, enhanced pod set |
|  | 0.5 (0.560) | Stature reduction, axillary bud development, leaf alteration, early pod set, enhanced pod set, inhibited pod development |
| L | 0.25 (0.28) | Leaf distortion, leaf alteration, early pod set, inhibited pod development |
|  | 0.1 (0.112) | Leaf distortion, leaf alteration, early pod set, inhibited pod development |
|  | 0.05 (0.056) | Leaf distortion, leaf alteration, early pod set |
|  | 2.5 (2.8) | Stem distortion, leaf inhibition, altered canopy, leaf distortion, axillary bud inhibition |
|  | 2.5 (2.8) | Stem distortion, leaf distortion, leaf inhibition, floral inhibition, axillary bud inhibition |
| Q | 1.0 (1.12) | Slight leaf burn, delayed pod set, stem distortion, inhibition of apical development, axillary bud inhibition, inhibited pod set |
|  | 0.25 (0.28) | Leaf distortion, leaf alteration, early pod set, enhanced pod set, inhibited pod development |
|  | 0.1 (0.112) | Early pod set, enhanced pod set, inhibited pod development |
|  | 0.05 (0.056) | Leaf distortion, leaf alteration, early pod set, inhibited pod development |
| E | 0.1 (0.112) | Leaf distortion, leaf alteration, early pod set, inhibited pod development |
|  | 0.05 (0.056) | Leaf distortion, leaf alteration, early pod set, inhibited pod development |
| R | 5.0 (5.6) | Slight leaf burn, stem distortion, inhibition of apical development, altered canopy, delayed pod set, axillary bud inhibition |
|  | 5.0 (5.6) | Moderate leaf burn, leaf inhibition, inhibition of apical development, axillary bud inhibition |

TABLE IX-continued

| Compound | RATE Lbs/Acre (kilos/hectare) | Results |
|---|---|---|
|  | 2.5 (2.8) | Moderate leaf burn, stem distortion, leaf inhibition, altered canopy, inhibition of apical development, inhibited pod set |
|  | 1.0 (1.12) | Stature reduction, stem distortion, leaf alteration, early pod set, axillary bud inhibition |
| T | 2.5 (2.8) | Stature reduction, leaf alteration, leaf inhibition, axillary bud inhibition, inhibited pod development |
|  | 1.0 (1.12) | Stature reduction, leaf distortion, leaf alteration, axillary bud inhibition, inhibited pod development |
|  | 0.5 (0.56) | Leaf distortion, leaf alteration, axillary bud inhibition, inhibited pod development |
|  | 0.25 (0.28) | Leaf alteration, early pod set, axillary bud inhibition, inhibited pod development |

Further plant growth regulatory activity was noted, especially leaf alteration and altered canopy, when soybean plants were treated in accordance with the procedure of Example 18.

EXAMPLE 18

A number of soybean plants are grown from seeds in plastic pots in the greenhouse for a period of 1 week at which time the plants are thinned to one plant per pot. When the second trifoliate leaf is fully expanded, the plants are treated with a solution of the active ingredient in acetone, water or N,N-dimethyl formamide. Aqueous Tween 20 is used as a surfactant.

When the fifth trifoliate leaf of the control is fully expanded, the treated plants are compared with the non-treated control plants and the observations recorded.

Table X, below, summarizes the results and observations made in accordance with Example 18 when the benzothiazoline compounds of the invention were utilized as the active ingredient.

TABLE X

| Compound | RATE Lbs/Acre (kilos/hectare) | Results |
|---|---|---|
| A | 2.5 (2.8) | Stem distortion, leaf alteration, altered canopy, thick leaf texture |
|  | 0.5 (0.56) | Leaf alteration, altered canopy, thick leaf texture |
|  | 0.1 (0.112) | Leaf alteration |
| G | 2.5 (2.8) | Stature reduction, chlorosis, epinasty, stem distortion, leaf distortion |
|  | 0.5 (0.56) | Stature reduction, chlorosis, stem distortion, leaf distortion, altered canopy |
|  | 0.1 (0.112) | Chlorosis, stem distortion, leaf distortion, altered canopy, thick leaf texture |
| V | 2.5 (2.8) | Stature reduction, chlorosis, epinasty, leaf distortion, altered canopy |
|  | 0.5 (0.56) | Stature reduction, chlorosis, stem distortion, leaf distortion, altered canopy |
|  | 0.1 (0.112) | Chlorosis, stem distortion, leaf distortion, altered canopy |
| H | 2.5 (2.8) | Stature reduction, epinasty, leaf distortion, inhibition of apical development, altered canopy |
|  | 0.5 (0.56) | Leaf distortion, stem distortion, altered canopy |
|  | 0.1 (0.112) | Leaf distortion, altered canopy |
| M | 2.5 (2.8) | Stature reduction, epinasty, leaf distortion, altered canopy |
|  | 0.5 (0.56) | Leaf distortion, stem distortion, altered canopy |
|  | 0.1 (0.112) | Stem distortion, altered canopy |
| I | 2.5 (2.8) | Stature reduction, chlorosis, epinasty, stem distortion, altered canopy |
|  | 0.5 (0.56) | Stem distortion, leaf distortion, altered canopy |
|  | 0.1 (0.112) | None |
| J | 2.5 (2.8) | Kill |
|  | 0.5 (0.56) | Stature reduction, chlorosis, stem distortion, leaf distortion, altered canopy |
|  | 0.1 (0.112) | Stem distortion, leaf distortion, altered canopy |
| N | 2.5 (2.8) | Stature reduction, epinasty, leaf distortion, inhibition of apical development, altered canopy |
|  | 0.5 (0.56) | Stem distortion, altered canopy |
|  | 0.1 (0.112) | Stem distortion, altered canopy |
| O | 2.5 (2.8) | Stature reduction, epinasty, leaf distortion, inhibition of apical development, altered canopy |
|  | 0.5 (0.56) | Stature reduction, stem distortion, leaf distortion, altered canopy |
|  | 0.1 (0.112) | Stem distortion, leaf distortion, altered canopy |
| P | 2.5 (2.8) | Stature reduction, chlorosis, epinasty, leaf distortion, altered canopy |
|  | 0.5 (0.56) | Chlorosis, stem distortion, altered canopy |
|  | 0.1 (0.112) | None |
| K | 2.5 (2.8) | Stature reduction, epinasty leaf alteration, altered canopy |
|  | 0.5 (0.56) | Stem distortion |
|  | 0.1 (0.112) | None |
| W | 2.5 (2.8) | Stem distortion, leaf alteration, leaf inhibition, altered canopy, thick leaf texture |
|  | 0.5 (0.56) | Leaf alteration, altered canopy, thick leaf texture |
|  | 0.1 (0.112) | Leaf alteration, thick leaf texture |
| X | 2.5 (2.8) | Stem distortion, leaf alteration, leaf inhibition, altered canopy, thick leaf texture |
|  | 0.5 (0.56) | Leaf alteration, leaf inhibition, altered canopy, thick leaf texture |
|  | 0.1 (0.112) | Leaf alteration, altered canopy, thick leaf texture |
| Y | 2.5 (2.8) | Stature reduction, stem distortion, leaf inhibition, leaf alteration, altered canopy, inhibition of apical development |
|  | 0.5 (0.56) | Stature reduction, stem distortion, leaf inhibition, leaf alteration, altered canopy, thick leaf texture |
|  | 0.1 (0.112) | Stem distortion, leaf alteration, leaf inhibition, altered canopy, thick leaf texture |
| T | 2.5 (2.8) | Leaf alteration, leaf inhibition, altered canopy, thick leaf texture |
|  | 0.5 (0.56) | Leaf alteration, altered canopy, thick leaf texture |
|  | 0.1 (0.112) | Leaf alteration |

Examples 16–18 illustrate that stature reduction of soybean plants is obtained when the benzothiazoline compounds of the invention are applied at relatively high rates, i.e. above about 2 pounds. At lower rates, however, the soybean plants undergo an alteration of their leaf shape and their canopy. This alteration of leaf shape and canopy enhances the penetration of sunlight into the canopy.

Percentage of full sunlight at various canopy heights was measured in plots of soybean plants treated with 2-oxo-3-benzothiazoline acetonitrile and compared with untreated controls. Table XI summarizes the results of said test.

TABLE XI

| Sensor | Percentage of Full Sunlight | |
|---|---|---|
| Height (cm) | Control | Treated Plants |
| 90 (Top of Canopy) | 100 | 100 |
| 60 | 27 | 64 |
| 30 | 17 | 22 |
| 2 | 14 | 16 |

The effect of altering the canopy of soybean plants was determined by comparing soybeans planted at several equidistant spacings. It is belived that no significant effect need be obtained by treating soybeans that were planted at great intervals because sunlight could reach the lower leaves between the plant rows. When the soybeans were planted close together, however, it would be necessary to open the canopy so that light could reach the lower leaves. Example 19 illustrates the results of the comparisons.

EXAMPLE 19

Williams soybeans are planted at various equidistant spacings at a rate of 6 seeds per foot (20 seeds per meter). After emergence, equidistant spacings is achieved by thinning and transplanting. The plants are treated with 2-oxo-3-benzothiazole acetonitrile at an early flowering stage using a hand-held $CO_2$ sprayer. The yield obtained is compared with that from untreated controlled plot. Results are illustrated by Table XII.

TABLE XII

| RATE Lbs/Acre (kilos/hectare) | Bean Yields Percentage of Control Equidistant Spacing (cm) | | | | | | |
|---|---|---|---|---|---|---|---|
| | 13 | 15 | 20 | 30 | 46 | 61 | 91 |
| 0.25 (0.28) | 132 | 110 | 106 | 104 | 105 | 108 | 84 |
| 0.50 (0.56) | 118 | 101 | — | 105 | 100 | 102 | 92 |

A preferred embodiment of the invention is those benzothiazoline compounds of the formula

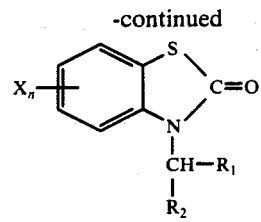

(II)

wherein $R_1$ is CN or COOH and agriculturally acceptable salts thereof. Specifically preferred are 2-oxo-3-benzothiazoline acetonitrile, 2-oxo-3-benzothiazoline acetic acid and its agriculturally acceptable salts.

By treating the plants with the benzothiazoline compounds of the invention, the period of fruit development is altered such that the number and/or size of the seeds is increased. It is believed that application of the compounds of the invention minimizes the deleterious effects of stress conditions to which the plants may be subjected. Such stress conditions may be induced by alteration of the plant population, length of growing period, and moisture conditions as well as others.

For example, irrigated plants were compared with nonirrigated plants and illustrated by Example 20.

EXAMPLE 20

Soybeans are planted at a rate of 150,000 seeds per acre in 20-inch (50.8 centimeters) row and treated with foliar application of 2-oxo-3-benzothiazoline acetonitrile at various rates using a tractor mounted boom sprayer. Each treatment is replicated at least 5 times and bean yields determined by harvesting the two center rows of each plot. These yields are then compared to the yield obtained in untreated control plots. Results are summarized in Table XIII.

TABLE XIII

| Soybean | Application Stage | RATE Lbs/Acre (kilos/hectare) | Bean Yield % of Control |
|---|---|---|---|
| Williams (irrigated) | early flower | 0.25 (0.28) | 98.6 |
| | early flower | 0.50 (0.56) | 99.5 |
| | early flower | 1.00 (1.12) | 93.5 |
| Wayne (non-irrigated) | preflower (1 week) | 0.25 (0.28) | 119.8 |
| | preflower (1 week) | 0.50 (0.56) | 117.4 |

Example 20 illustrates that when a stress factor, such as lack of moisture, is eliminated the non-treated control was able to produce high yields. When subjected to the same stress factor, however, the controls yield was significantly below that of the treated plants.

The table below illustrates the yields obtained when soybeans were planted at various times. Those planted in May were subjected to an ideal amount of rainfall and normal sunlight. Those planted in June were subjected to a reduced growing cycle (less daylight). The data below represents the mean of several tests in which both the rate and date of chemical application varied.

TABLE XIV

| | Yield Bushels/Acre (kg/hectare) | | |
|---|---|---|---|
| Date Planted | Control | Treated with 2-oxo-3-benzothiazoline acetonitrile | % of Control |
| 5-15 | 59.5 (5.16) | 52.9 (4.59) | 89 |
| 5-22 | 53.0 (4.59) | 52.3 (4.55) | 98 |
| 6-3 | 62.0 (5.38) | 63.0 (5.48) | 102 |
| 6-13 | 44.0 (3.83) | 52.0 (4.52) | 118 |

TABLE XIV-continued

| | Yield Bushels/Acre (kg/hectare) | | |
|---|---|---|---|
| Date Planted | Control | Treated with 2-oxo-3-benzothiazoline acetonitrile | % of Control |
| 6-23 | 46.0 (4.00) | 52.0 (4.52) | 113 |
| 7-3 | 41.0 (3.56) | 44.0 (3.83) | 107 |

The above data indicates that when soybean plants are subjected to a stress condition, e.g. delayed planting leading to a reduced growing cycle, application to the plants of the compounds of the invention helps minimize the deleterious effects of said stress condition.

Although this invention has been described with respect to specific modification, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of increasing the yield of soybean plants which comprises treating said soybean plants with an effective non-lethal amount of a compound of the formula

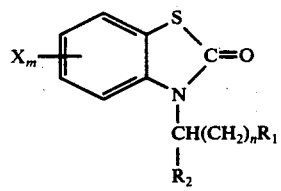

wherein X is halo; $m$ is 0 or 1;

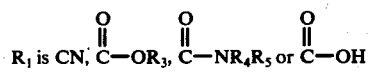

$R_1$ is CN, $\overset{O}{\underset{\|}{C}}-OR_3$, $\overset{O}{\underset{\|}{C}}-NR_4R_5$ or $\overset{O}{\underset{\|}{C}}-OH$ and agriculturally acceptable salts thereof; $R_2$ is H, CN, lower alkyl or

$\overset{O}{\underset{\|}{C}}-OR_3$;

$R_3$ is lower alkyl; $R_4$ and $R_5$ are independently H, alkyl or when taken together with the nitrogen molecule form a heterocyclic having up to 8 carbon atoms, inclusive; and $n$ is 0 or 2; provided that $R_2$ is

$\overset{O}{\underset{\|}{C}}-OR_3$ only when $R_1$ is $\overset{O}{\underset{\|}{C}}-OR_3$ and $n$ is 0.

2. A method according to claim 1 wherein X is chloro; $R_1$ is CN or

$\overset{O}{\underset{\|}{C}}-OH$ and agriculturally acceptable salts thereof; and $R_2$ is H.

3. A method according to claim 2 wherein $m$ is 0 and $n$ is 0.

4. A method according to claim 1 wherein said compound is 2-oxo-3-benzothiazoline acetonitrile 5. A method according to claim 1 wherein said compound is 2-oxo-3-benzothiazoline butyronitrile.

6. A method according to claim 1 wherein said compound is 2-oxo-3-benzothiazoline acetic acid and agriculturally acceptable salts thereof.

7. A method for reducing the stature of soybean plants which comprises treating said soybean plants with a stature reducing amount of a compound of the formula

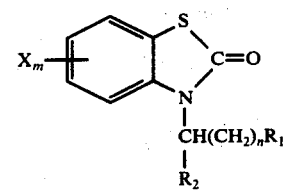

wherein X is halo; $m$ is 0 or 1;

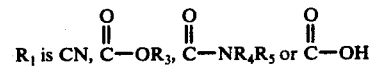

$R_1$ is CN, $\overset{O}{\underset{\|}{C}}-OR_3$, $\overset{O}{\underset{\|}{C}}-NR_4R_5$ or $\overset{O}{\underset{\|}{C}}-OH$ and agriculturally acceptable salts thereof; $R_2$ is H, CN, lower alkyl or

$\overset{O}{\underset{\|}{C}}-OR_3$;

$R_3$ is lower akyl; $R_4$ and $R_5$ are independently H, alkyl or when taken together with the nitrogen molecule form a heterocyclic having up to 8 carbon atoms, inclusive; and $n$ is 0 or 2; provided that $R_2$ is

$\overset{O}{\underset{\|}{C}}-OR_3$ only when $R_1$ is $\overset{O}{\underset{\|}{C}}-OR_3$ and $n$ is 0.

8. A method according to claim 7 wherein X is chloro; $R_1$ is CN or

$\overset{O}{\underset{\|}{C}}-OH$ and agriculturally acceptable salts thereof; and $R_2$ is H.

9. A method according to claim 8 wherein $m$ is 0 and $n$ is 0.

10. A method according to claim 7 wherein said compound is 2-oxo-3-benzothiazoline acetonitrile.

11. A method according to claim 7 wherein said compound is 2-oxo-3-benzothiazoline butyronitrile.

12. A method according to claim 7 wherein said compound is 2-oxo-3-benzothiazoline acetic acid and agriculturally acceptable salts thereof.

13. A method according to claim 7 wherein said compound is applied at a rate above 2.24 kilos per hectare.

14. A method for altering the canopy of soybean plants which comprises treating said soybean plants with a canopy altering amount of a compound of the formula

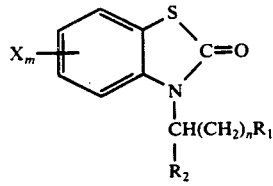

wherein X is halo; $m$ is 0 or 1;

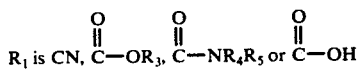

and agricultrurally salts thereof; $R_2$ is H, CN, lower alkyl or

$R_3$ is lower alkyl; $R_4$ and $R_5$ are independently H, alkyl or when taken together with the nitrogen molecule form a heterocyclic having up to 8 carbon atoms, inclusive; and $n$ is 0 or 2 provided that $R_2$ is

only when $R_1$ is

and $n$ is 0.

15. A method according to claim 14 wherein X is chloro; $R_1$ is CN or $$\overset{O}{\underset{\|}{C}}-OH$$

and agriculturally acceptable salts thereof; and $R_2$ is H.

16. A method according to claim 15 wherein $m$ is 0 and $n$ is 0.

17. A method according to claim 14 wherein said compound is 2-oxo-3-benzothiazoline acetonitrile.

18. A method according to claim 14 wherein said compound is 2-oxo-3-benzothiazoline butyronitrile.

19. A method according to claim 14 wherein said compound is 2-oxo-3-benzothiazoline acetic acid and agriculturally acceptable salts thereof.

20. A method according to claim 14 wherein said compound is applied at a rate below 3.36 kilos per hectare.

* * * * *